US012380524B2

(12) United States Patent
Lakkaraju et al.

(10) Patent No.: US 12,380,524 B2
(45) Date of Patent: Aug. 5, 2025

(54) METHODS, DEVICES, AND SYSTEMS FOR PROVIDING CONFINEMENT FLEXIBILITY TO INDIVIDUALS THAT ARE UNDER TWENTY-FOUR-HOUR-SEVEN-DAY-A-WEEK (24/7) SUPERVISION AND/OR ARE REQUIRED TO BE INCARCERATED

(71) Applicant: MLINZI Group LLC, Raleigh, NC (US)

(72) Inventors: Sita Lakkaraju, Raleigh, NC (US); Vindhya Kunduru, Hillsboro, OR (US)

(73) Assignee: MLINZI Group LLC, Raleigh, NC (US)

(*) Notice: Subject to any disclaimer, the term of this patent is extended or adjusted under 35 U.S.C. 154(b) by 182 days.

(21) Appl. No.: 18/326,294

(22) Filed: May 31, 2023

(65) Prior Publication Data

US 2023/0385974 A1 Nov. 30, 2023

Related U.S. Application Data

(60) Provisional application No. 63/347,326, filed on May 31, 2022.

(51) Int. Cl.
*G06Q 50/26* (2024.01)
*G08B 21/02* (2006.01)
*G16H 20/70* (2018.01)
*G16H 40/67* (2018.01)

(52) U.S. Cl.
CPC ........... *G06Q 50/265* (2013.01); *G06Q 50/26* (2013.01); *G08B 21/02* (2013.01); *G16H 20/70* (2018.01); *G16H 40/67* (2018.01)

(58) Field of Classification Search
None
See application file for complete search history.

(56) References Cited

U.S. PATENT DOCUMENTS

| 6,054,928 | A | * | 4/2000 | Lemelson | .......... | G08B 21/0423 |
| | | | | | | 455/100 |
| 2021/0084451 | A1 | * | 3/2021 | Williams | ................ | H04W 4/38 |
| 2022/0058683 | A1 | * | 2/2022 | Deberry | ............ | G06Q 30/0208 |
| 2022/0207635 | A1 | * | 6/2022 | Hughes | ................... | E05B 45/00 |

* cited by examiner

*Primary Examiner* — Thomas S McCormack
(74) *Attorney, Agent, or Firm* — NK Patent Law

(57) ABSTRACT

This disclosure presents methods, systems, and devices for providing confinement flexibility via virtual reality (VR) and/or augmented reality (AR) to individuals that are incarcerated and or required to be incarcerated. According to one embodiment, a method is disclosed that includes using a computing device for receiving a first rule set associated with a first entity and the first rule set is associated with the individual over a time period, receiving a second rule set associated with a second entity and the second entity is responsible for enforcement of the first rule set, receiving a third rule set associated with an environment in which the individual is allowed to be located during the time period, determining a first set of actions to be implemented by a wearable computing device that is in physical contact with the individual, and transmitting over a wireless network the first set of actions to the wearable computing device.

20 Claims, 6 Drawing Sheets

FLOW DIAGRAM
100

METHODS, DEVICES, AND SYSTEMS FOR PROVIDING CONFINEMENT FLEXIBILITY TO INDIVIDUALS THAT ARE UNDER TWENTY-FOUR-HOUR-SEVEN-DAY-A-WEEK (24/7) SUPERVISION AND/OR ARE REQUIRED TO BE INCARCERATED

PRIORITY CLAIM

This application claims priority to U.S. Provisional Patent Application Ser. No. 63/347,326 filed May 31, 2022, entitled "METHODS, DEVICES, AND SYSTEMS FOR PROVIDING CONFINEMENT FLEXIBILITY TO INDIVIDUALS THAT ARE UNDER TWENTY-FOUR-HOUR-SEVEN-DAY-A-WEEK (24/7) SUPERVISION AND/OR ARE REQUIRED TO BE INCARCERATED". The disclosure of the aforementioned application is incorporated herein by reference in its entirety.

TECHNICAL FIELD

The present invention relates generally to virtual reality (VR) systems and augmented reality (AR) systems. More specifically, the invention relates to providing confinement flexibility via VR devices and AR devices to individuals that are incarcerated and/or under twenty-four-hour-seven-day-a-week (24/7) supervision, including the software and additional hardware involved in the working and management of the VR systems and the AR systems in a confinement setting.

BACKGROUND

Over the past several decades, incarceration rates have more than tripled in the United States. Individuals (e.g., inmates) may be short-term incarcerated or long-term incarcerated in a county facility, a state facility, a federal facility, a private facility, and or the like. Additionally, individuals may be incarcerated under house arrest and/or the like. Incarceration can deter these individuals from committing future crimes and incarceration can provide rehabilitative care. For example, rehabilitative care may include wellness programs and education for the individuals (including vocational training). However, options for providing rehabilitative care can be limited within such incarceration facilities. Additionally, children having one or more parents incarcerated suffer great developmental issues, not to mention the loss of income for the family. Other incarceration issues include lack of privacy that can further exacerbate the mental health of an individual, gang activity, and self-harm including suicide.

As such new methods, systems, and devices for providing confinement flexibility for individuals that are incarcerated and/or required to be incarcerated are needed.

SUMMARY

This disclosure presents methods, systems, and devices for providing confinement flexibility via virtual reality (VR) and/or augmented reality (AR) to individuals that are incarcerated and or required to be incarcerated. Additionally, these disclosed methods, systems, and devices apply to individuals that are under twenty-four-hour-seven-day-a-week (24/7) supervision. These individuals may be resident to psychiatric facility such as a long-term facility, a psych ward of a hospital, a respite facility, a memory-care facility, a group home, or the like.

According to one embodiment, a method is disclosed that includes using at least one computing device for (1) receiving a first rule set associated with a first entity and the first rule set is associated with the individual over a time period, (2) receiving a second rule set associated with a second entity and the second entity is responsible for enforcement of the first rule set, (3) receiving a third rule set associated with an environment in which the individual is allowed to be located during the time period, (4) determining a first set of actions to be implemented by a wearable computing device that is in physical contact with the individual, and (5) transmitting over a wireless network the first set of actions to the wearable computing device.

In some embodiments, the wearable computing device may be attached to the individual prior to a beginning of the time period and the wearable computing device may be removed from the individual after an ending of the time period. The time period may be associated with an incarceration period of the individual determined by a judicial branch of government.

In some embodiments, the method may further include using the at least one computing device for receiving a fourth rule set associated with a therapy plan for the individual. In further embodiments, the therapy plan may be configured to treat a psychological condition, a behavioral health issue, and/or the like. The therapy plan may also be configured to provide a teletherapy session from a licensed and/or certified therapist.

In some embodiments, the therapy plan may be further configured to treat at least one category of the Diagnostic and Statistical Manual of Mental Disorders, Fifth Edition, Text Revision (DSM-5-TR). In further embodiments, the therapy plan may be configured to treat a trauma and stressor related disorder. In still further embodiments, the therapy plan may be configured to treat an obsessive-compulsive disorder. In still further embodiments, the therapy plan may be configured to treat an anxiety disorder.

In some embodiments, the therapy plan may be configured to treat and/or reduce symptoms associated with one or more medical disorders. In still other embodiments, the therapy plan may be configured to treat one or more sexual disorders. In still other embodiments, the therapy plan may be configured to treat family and/or relationship issues associated with the individual and others.

In some embodiments, the first set of actions may be determined based on the first rule set, the second rule set, the third rule set and/or the fourth rule set.

In some embodiments, the first entity may be associated with a judicial branch of government. In further embodiments, the first entity may be associated with a state court system. In other embodiments, the first entity may be associated with a federal court system. In further embodiments, the time period may be associated with an incarceration period of the individual determined by the judicial branch of government.

In some embodiments, the first rule set may be associated with a criminal sentence imposed on the individual by the judicial branch of government. In further embodiments, the criminal sentence may include incarceration of the individual during the time period.

In some embodiments, the second entity may be associated with an executive branch of government. In further embodiments, the second entity may be associated with a state corrections system. In other embodiments, the second entity may be associated with a federal corrections system branch of government.

In some embodiments, the environment may include a perimeter. In further embodiments, the perimeter may be associated with an incarceration of an individual. In still embodiments, the first set of actions may include a geometric coordinate located within the perimeter.

In some embodiments, the perimeter may approximate a geometric shape. In further embodiments, the geometric shape may be at least one of a polygon and an oval.

In some embodiments, wherein the perimeter may have a value between 30 meters and 300 meters. In other embodiments, the perimeter may have a value between 300 meters and 3000 meters. In still other embodiments, the perimeter may have a value between 3000 meters and 30,000 meters. In still other embodiments, the perimeter may have a value between 30,000 meters and 300,000 meters. In still other embodiments, the perimeter may have a value less than 30 meters or greater than 300,000 meters.

In some embodiments the method may further include using the at least one computing device for receiving a proximity alert when the wearable computing device detects a proximity to the perimeter.

In some embodiments the method may further include using the at least one computing device for receiving a tamper alert when the wearable computing device detects localized tampering.

In some embodiments, the wearable computing device may include a virtual reality (VR) device.

In some embodiments, the wearable computing device may include an augmented reality (AR) device.

In some embodiments, the first set of actions may include a profile associated with the individual. In further embodiments, the profile may include behavioral data and medical data associated with the individual. In still further embodiments, the behavioral data may include generic behavioral data associated with a personality type. In still further embodiments, the behavioral data may include individual specific behavioral data associated with the individual. In still further embodiments, the medical data may include generic medical data associated with a patient type. In certain embodiments, the medical data may include individual specific medical data associated with the individual.

In some embodiments, the profile may further include environmental data associated with the environment in which the individual is allowed to be located during the time period.

In some embodiments, the wireless network may be a wide area network (WAN).

In some embodiments, the wireless network may be a cellular network. In further embodiments, the cellular network may include a 3G network, a 4G network, a 5G network, and/or the like.

In some embodiments, the wireless network may be a wireless local area network (WLAN). In further embodiments, the WLAN may be compliant to at least one version of an Institute of Electrical and Electronics Engineers (IEEE) 802.11 communication standard.

In some embodiments, the wireless network may be a wireless personal area network (WPAN). In further embodiments, the WPAN may be compliant to at least one version of a Bluetooth® communication standard.

In some embodiments the method may further include attaching the wearable computing device to the individual prior to a beginning of the time period.

In further embodiments, a sworn officer of an executive branch of government may be responsible for attaching the wearable computing device to the individual prior to the beginning of the time period.

In some embodiments the method may further include removing the wearable computing device from the individual after an ending of the time period.

In further embodiments, a sworn officer of an executive branch of government may be responsible for removing the wearable computing device from the individual after the ending of the time period.

According to another embodiment, a computing device is disclosed that includes a memory and a processor is configured to perform a method. The method includes (1) receiving a first rule set associated with a first entity and the first rule set is associated with the individual over a time period, (2) receiving a second rule set associated with a second entity and the second entity is responsible for enforcement of the first rule set, (3) receiving a third rule set associated with an environment in which the individual is allowed to be located during the time period, (4) determining a first set of actions to be implemented by a wearable computing device that is in physical contact with the individual, and (5) transmitting over a wireless network the first set of actions to the wearable computing device. In some embodiments the computing device may include multiple computing devices with multiple memories and multiple processors.

According to another embodiment, a non-transitory computer readable medium is disclosed that includes a plurality of machine-readable instructions which when executed by one or more processors of one or more computing devices are adapted to perform a method for providing confinement flexibility to an individual. The method includes (1) receiving a first rule set associated with a first entity and the first rule set is associated with the individual over a time period, (2) receiving a second rule set associated with a second entity and the second entity is responsible for enforcement of the first rule set, (3) receiving a third rule set associated with an environment in which the individual is allowed to be located during the time period, (4) determining a first set of actions to be implemented by a wearable computing device that is in physical contact with the individual, and (5) transmitting over a wireless network the first set of actions to the wearable computing device.

According to another embodiment, a method is disclosed for providing confinement flexibility using VR and/or AR to an individual that is incarcerated and or required to be incarcerated. The method includes a sworn officer of an executive branch of government attaching a wearable computing device (including VR technology and/or AR technology) to the individual prior to a beginning of a time period. The method further includes removing the wearable computing device at an ending of the time period. The wearable computing device may be removed by the individual, the sworn officer, and/or another sworn officer at the ending of the time period. The time period is associated with an incarceration period of the individual determined by a judicial branch of government.

The method further includes using at least one computing device (e.g., one or more servers) for receiving a first rule set associated with a first entity and the first rule set is associated with the individual over a time period; receiving a second rule set associated with a second entity and the second entity is responsible for enforcement of the first rule set; receiving a third rule set associated with an environment in which the individual is allowed to be located during the time period; and receiving a fourth rule set associated with a therapy plan for the individual. The therapy plan is configured to treat a psychological condition and/or a behavioral health issue of the individual.

The first entity is associated with the judicial branch of government and the second entity is associated with an executive branch of government. The first rule set is further associated with a criminal sentence imposed on the individual by the judicial branch of government. The environment includes a perimeter and the perimeter is associated with the incarceration period of the individual.

The method further includes further using the at least one computing device for determining (using the first the first through fourth rule sets) a first set of actions to be implemented by a wearable computing device that is in physical contact with the individual; and transmitting over a wireless WAN the first set of actions to the wearable computing device. The first set of actions includes a geometric coordinate located within the perimeter and a profile associated with the individual. The profile includes behavioral data and medical data associated with the individual. The profile also includes environmental data associated with the environment in which the individual is allowed to be located during the time period.

The method further includes further using the at least one computing device for receiving a proximity alert when the wearable computing device detects a proximity to the perimeter and receiving a tamper alert when the wearable computing device detects localized tampering.

The features and advantages described in this summary and the following detailed description are not all-inclusive. Many additional features and advantages will be apparent to one of ordinary skill in the art in view of the drawings, specification, and claims presented herein.

DETAILED DESCRIPTION

Figure 1:
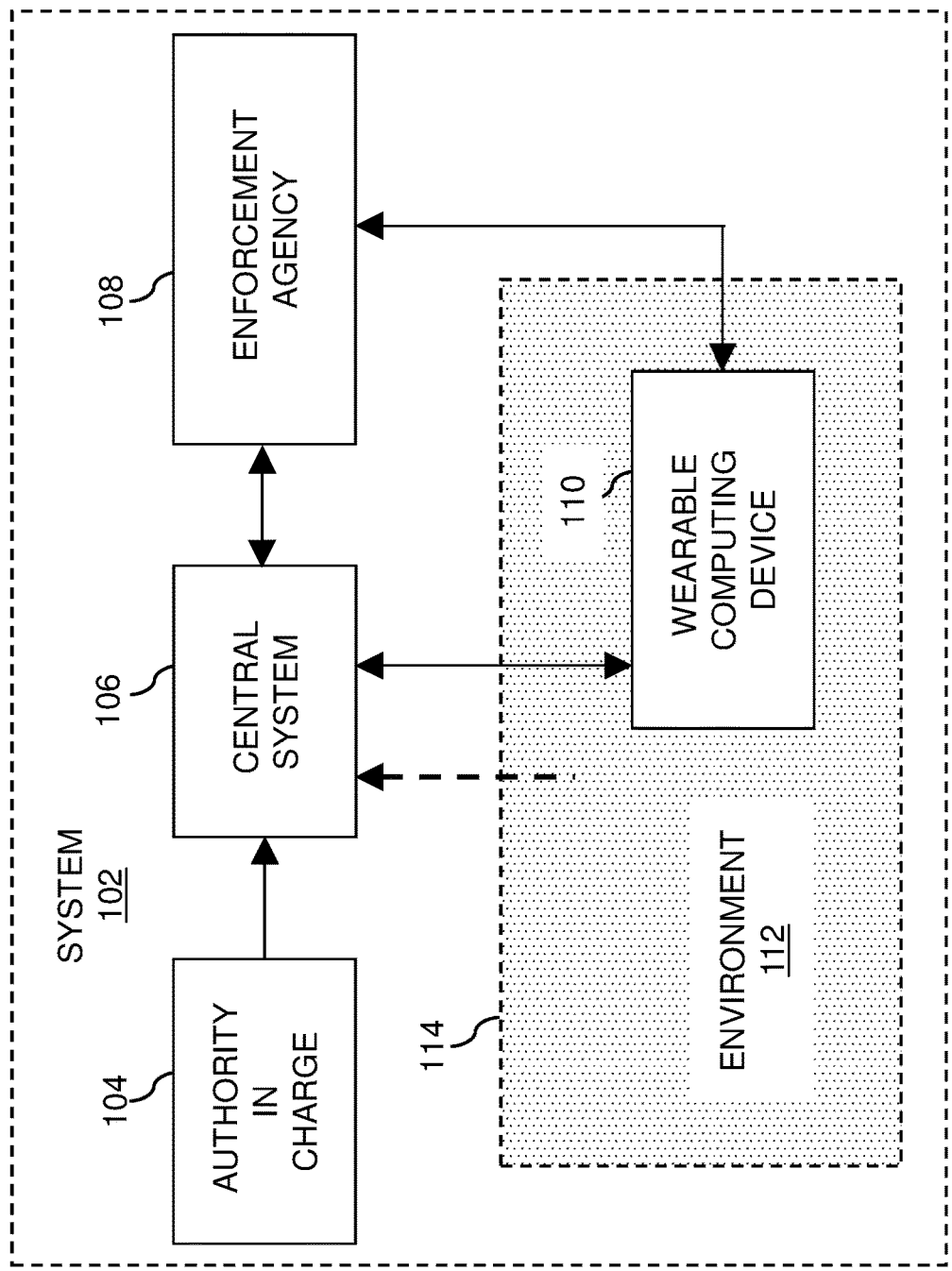
FIG. 1 depicts a block diagram illustrating a system including a central system and a wearable computing device for providing confinement flexibility via virtual reality (VR) and/or augmented reality (AR) in accordance with embodiments of the present disclosure.

The following description and drawings are illustrative and are not to be construed as limiting. Numerous specific details are described to provide a thorough understanding of the disclosure. However, in certain instances, well-known or conventional details are not described in order to avoid obscuring the description.

Reference in this specification to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not for other embodiments.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way.

Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only, and is not intended to further limit the scope and meaning of the disclosure or of any exemplified term. Likewise, the disclosure is not limited to various embodiments given in this specification.

Unless otherwise indicated, all numbers expressing quantities of components, conditions, and so forth used in the specification and claims are to be understood as being modified in all instances by the term "about". Accordingly, unless indicated to the contrary, the numerical parameters set forth in the instant specification and attached claims are approximations that can vary depending upon the desired properties sought to be obtained by the presently disclosed subject matter.

Without intent to limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, all technical and scientific terms used herein have the same meaning as commonly understood by one of ordinary skill in the art to which this disclosure pertains. In the case of conflict, the present document, including definitions, will control.

Disclosed herein are methods, devices, and systems for providing confinement flexibility via virtual reality (VR) and/or augmented reality (AR) to individuals that are incarcerated or to individuals that are under twenty-four-hour-seven-day-a-week 24/7 supervision. FIG. 1 depicts a block diagram 100 illustrating a system 102 in accordance with embodiments of the present disclosure. The system 102 includes an authority in charge 104 (i.e. a first entity) communicatively coupled with a central system 106. The central system 106 includes one or more computing devices and is communicatively coupled with an enforcement agency 108 (i.e. a second entity) and a wearable computing device 110. The wearable computing device 110 is attached to an individual (not shown in FIG. 1) within an environment 112 having a perimeter 114. The individual may be required to be located in the environment 112 during a required time period. For example, the system 102 may also provide a virtual prison for the individual (e.g., VR prisoner).

The wearable computing device 110 may include any device that can be mounted, attached, and/or affixed to the individual being provided confinement flexibility. These devices include but are not limited to goggles, eyewear such as contacts, monitoring devices, devices for restricting sensory environment, and/or the like.

The visual environment seen by each individual being provided confinement flexibility and the interaction allowed for each individual with the environment 112 are coded in the central system 106 as rules. Rules are established by the authority in charge 104. The authority in charge 104 is also responsible for of ongoing maintenance of the rules. The enforcement agency 108 is the entity charged with implementing the rules set forth by the authority in charge 104.

Once the individual is fitted with the wearable computing device 110, the individual's physical coordinates and actions are monitored 24/7 by the central system 106. As such, the wearable computing device 110 must be worn 24/7 by the individual and can be removed only by the enforcement agency 108 as ordered by the authority in charge 104. A sensor within the wearable computing device 110 is able to detect whether the wearable computing device 110 is correctly installed on the individual on an ongoing basis. Alerts are sent to the central system 106 regarding the status of the wearable computing device 110.

The central system 106 controls the entire visual field of the individual. Each individual has a customized experience specific to the individual as dictated by the authority in charge 104. The visual environment is dynamically controlled and derived from VR environments and/or AR environments. The individual's physical coordinates are also restricted using VR and AR. As such, the authority in charge 104 is able to simulate an environment for the individual which is much different from physical reality. The individual may be in a public area shared with other people but their view would be very different from that of the individual.

Areas, elements and parties, static and dynamic, in the visual environment that the individual does not have access to, will be depicted as impenetrable obstacles. Interaction with unauthorized areas, elements or parties, or any movements made outside of the purveyance of the visual field will result in corrective action taken by the central system 106 according to the rules provided by the authority in charge 104. Corrective action could range from visual and audio alerts, all the way to a complete audio and visual sensory deprivation resulting in complete control of individual's actions. When necessary, the central system 106 may deactivate the wearable computing device 110 and completely restore the individual's field of vision to physical reality.

The authority in charge 104 is able to send audio and visual messages to the individual. Additionally, the authority in charge 104 can send instructions to the individual to perform tasks as required. Tasks could involve interaction with other individuals as authorized by the authority in charge 104. The individual could participate in tasks and programs, either mandated or voluntarily. The programs could have learning outcomes, be part of rehabilitation, and/or for recreation. The programs would all be all accomplished through the wearable computing device 110.

Now disclosed is a typical day in the life of the individual (e.g. a VR prisoner) with the wearable computing device 110 attached. Any object (e.g., living or otherwise) that the central system 106 does not want the individual to see is displayed as a "grey box" in the individual's view.

The individual wakes up in a designated living area (e.g., a home base), and "checks in" with the central system 106 for a list of assignments for the day. Throughout the night, the central system 106 had been sensing the individual's irises for authentication every time the individual's eyes are opened. The individual asks the central system 106 for directions to the nearest bathroom, and follows instructions provided from the central system 106. After freshening up, the individual heads towards the location of their first assignment.

Walking on the street, the individual is presented by the central system 106 with arrows for directing movement. The individual sees many dark grey "boxes" of various sizes, with some moving and some static. By mistake, the individual turns right towards the upcoming street. A message is then received to "turn left." A little late to react, and while avoiding a moving grey box, the individual ends up turning all the way right. The individual's view is replaced by a dark screen with the message "turn around." The street was off-limits per the rules from the authority in charge 104. The individual turns around and the display is restored. The individual then continues on and stops at a food vending machine. Using a wrist band, the individual purchases breakfast and eats at a bench. The individual recognizes another person on the bench (e.g., a fellow VR prisoner) who is also headed to the same training class next. After eating and following directions issued by the central system 106, they both go to a training center to learn computer programming. After the training session, the individual looks around but the other person is no longer visible.

The central system 106 presents a few options for the day's work. The individual chooses to remove weeds at a community garden across town. Following directions, the individual waits at a bus stop for public transportation. The individual sees small "grey boxes" moving fast and colliding. One of the boxes gets closer. The central system 106 issues a warning heard externally. All the grey boxes then move away. The bus arrives and the individual gets on. The individual gets off the bus and walks into the office at the garden. The garden employee at the front desk checks-in the individual and the central system 106 directs the individual to the right area. After a few hours, the individual takes the bus back as instructed to a cafeteria at a shelter for a meal. The grey boxes provide one method of occlusion of unapproved living entities and/or unliving entities from the individual. Occlusion may be accomplished by superimposition of virtual objects (e.g., the grey boxes), by pixelation, and/or the like using the capability of VR and AR technologies. In further embodiments, the grey boxes may be a different color (e.g., red, blue, green, and/or the like). Additionally, the grey boxes may be presented as other geometric shapes (e.g., spheres, cylinders, cones, spheres, and/or the like) and may also include pixelation. In still other embodiments, the living entities and/or unliving entities may be represented to the individual as obscured images using solid or pixelated techniques as known in the art.

The individual walks to a nearby location (i.e. a designated area) to meet a group of fellow individuals (e.g., prisoners). This is a regular meeting organized and facilitated by the central system 106 for social rehabilitation. Inside the room, the VR/AR experience is replaced by reality as seen without any devices.

The individual is then directed back to their designated home base. The individual participates in rehabilitation programs, some voluntary and some mandatory. The individual then meets with a correctional officer virtually to review their progress. If the individual has miss-stepped (e.g., going on to disallowed streets or the like) they are so told and of any possible consequences.

Depending on the severity of the crime, the sentence, and/or the penal code in effect; the individual may be mandated to wear a certain type of clothing. The certain type of clothing may or may not include sensors communicatively coupled with the wearable computing device 110.

An outward facing camera on the wearable computing device 110 (similar to a "bodycam" worn by police) may be used to monitor, alert, and keep the individual safe from attacks while they are in public places: The public is expected to keep a safe distance from the individual and an alert is issued if that is violated. An emergency call is placed immediately when activity that is deemed threatening against the individual is observed.

Figure 2:
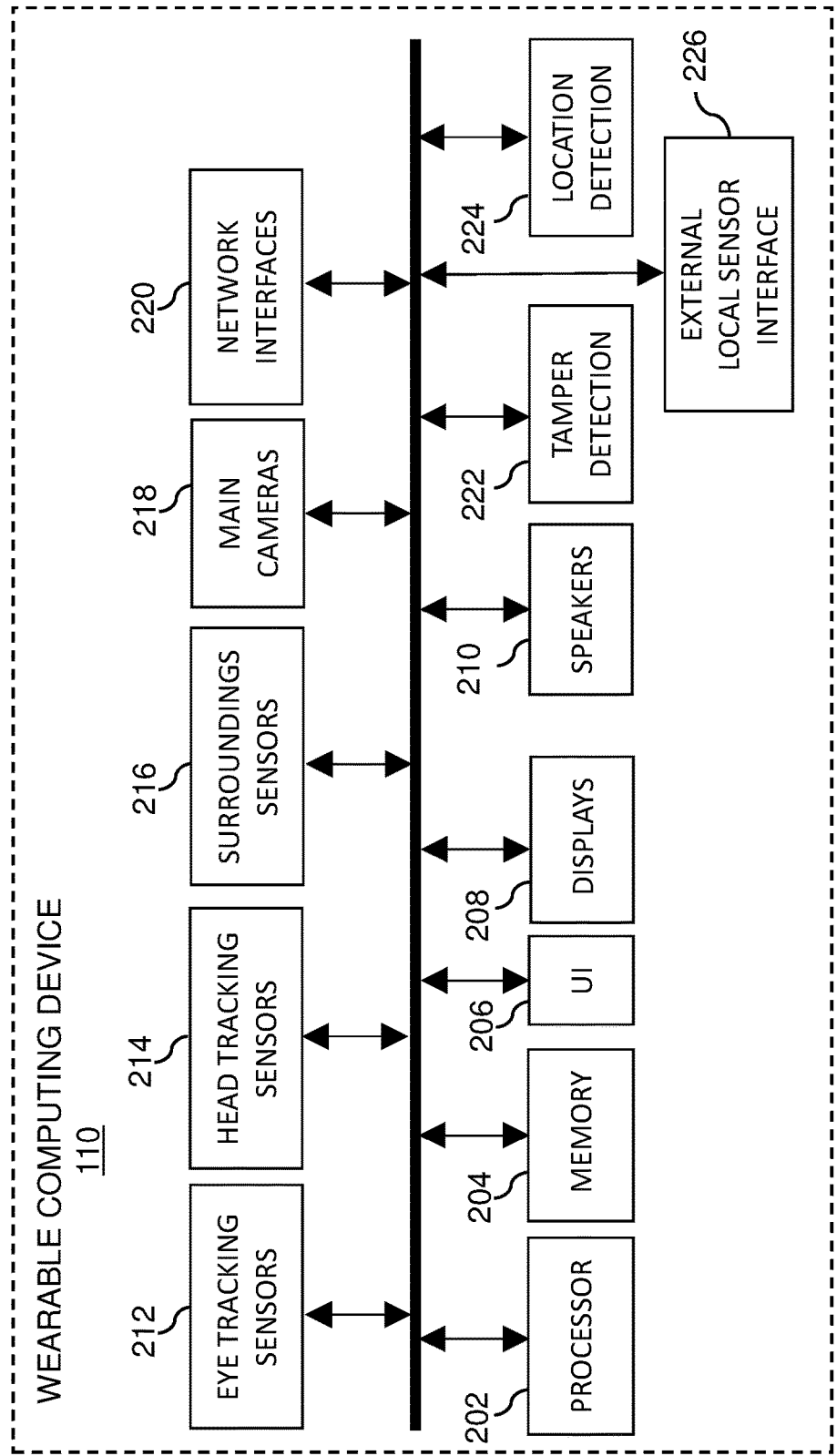
FIG. 2 depicts a block diagram of the wearable computing device of FIG. 1 in accordance with embodiments of the present disclosure.

FIG. 2 depicts a block diagram 200 illustrating the wearable computing device 110 of FIG. 1 for providing confinement flexibility via VR and/or AR in accordance with embodiments of the present disclosure. The wearable computing device 110 includes a processor 202, a memory 204, a user interface (UI) 206, displays 208, speakers 210, eye tracking sensors 212, head tracking sensors 214, surroundings sensors 216, main cameras 218, and network interfaces 220.

The processor 202 may be the Qualcomm Snapdragon 835 System on Chip (SoC) or the like. In some embodiments the memory 204 or a portion of the memory 204 may be integrated with the processor 202. The memory 204 may include a combination of volatile memory (e.g. random access memory) and non-volatile memory (e.g. flash memory). The UI 206 may include a touchpad display.

The displays 208 may include left and right displays for each eye of an individual wearing the wearable computing device 110. In some embodiments, the displays 208 may have a resolution of 1080×1200 per eye or greater. In further embodiments, the displays 208 may have a resolution of 1440×1600 per eye or greater.

The speakers 210 may be positioned within the wearable computing device 110. In other embodiments, the speakers 210 may be provided as earbuds or headphones. Connections to the speakers 210 may be wired or wireless (e.g., Bluetooth®).

The eye tracking sensors 212 may include cameras co-positioned with the displays 208. The head tracking sensors 214 may include a three-axis gyroscope sensor, an accelerometer sensor, a proximity sensor, or the like. The surroundings sensors 216 may include cameras positioned at a plurality of angles to view an outward circumference of the wearable computing device 110. The main cameras 218 may include high resolution cameras configured to provide main left eye and right eye views to the user.

The network interfaces 220 may include a plurality of wireless radios. The wireless radios may include wide area network (WAN) radios, local area network (LAN) radios, and personal area network (PAN) radios. The WAN radios may include 2G, 3G, 4G, and/or 5G circuitry. The LAN radios may include Wi-Fi technologies such as 802.11a, 802.11b/g/n, and/or 802.11ac circuitry. The PAN radios may include Bluetooth® circuitry and/or Bluetooth Low Energy (BLE®) circuitry.

The wearable computing device 110 also includes tamper detection 222, location detection 224, and external local sensor interface 226. The tamper detection 222 is configured to detect if an individual removes or attempt so remove the wearable computing device 110. The location detection 224 may include a GPS receiver for identifying and/or verifying the present location of the wireless computing device 110.

The external local sensor interface 226 is configured to communicate with external sensors to the wearable computing device 110. For example, a VR or AR body suit, health monitoring, sensors, and or the like. Additionally, the PAN radios may be used for this purpose.

The wearable computing device 110 may also include a rechargeable battery and recharging circuitry (not shown in FIG. 2). The recharging circuitry may be wired or wireless.

The wearable computing device may contain program instructions for algorithms and features associated with VR wearable devices and AR wearable devices. The VR wearable devices may include Oculus Quest VR headsets, Oculus Quest 2 VR headsets, Oculus Go headsets, Pico Neo 1 VR headsets, Pico Neo 2 VR headsets, Pico Neo 3 VR headsets, Pico Goblin 1 VR headsets, Pico Goblin 2 VR headsets, HTC VIVE Focus VR headsets, HTC VIVE Focus Plus VR headsets, HTC VIVE Focus 3 VR headsets, and/or the like. The AR wearable devices may include Hololens 1 AR headsets, Hololens 2 AR headsets, Magic Leap 1 AR headsets, and/or the like.

Figure 3:
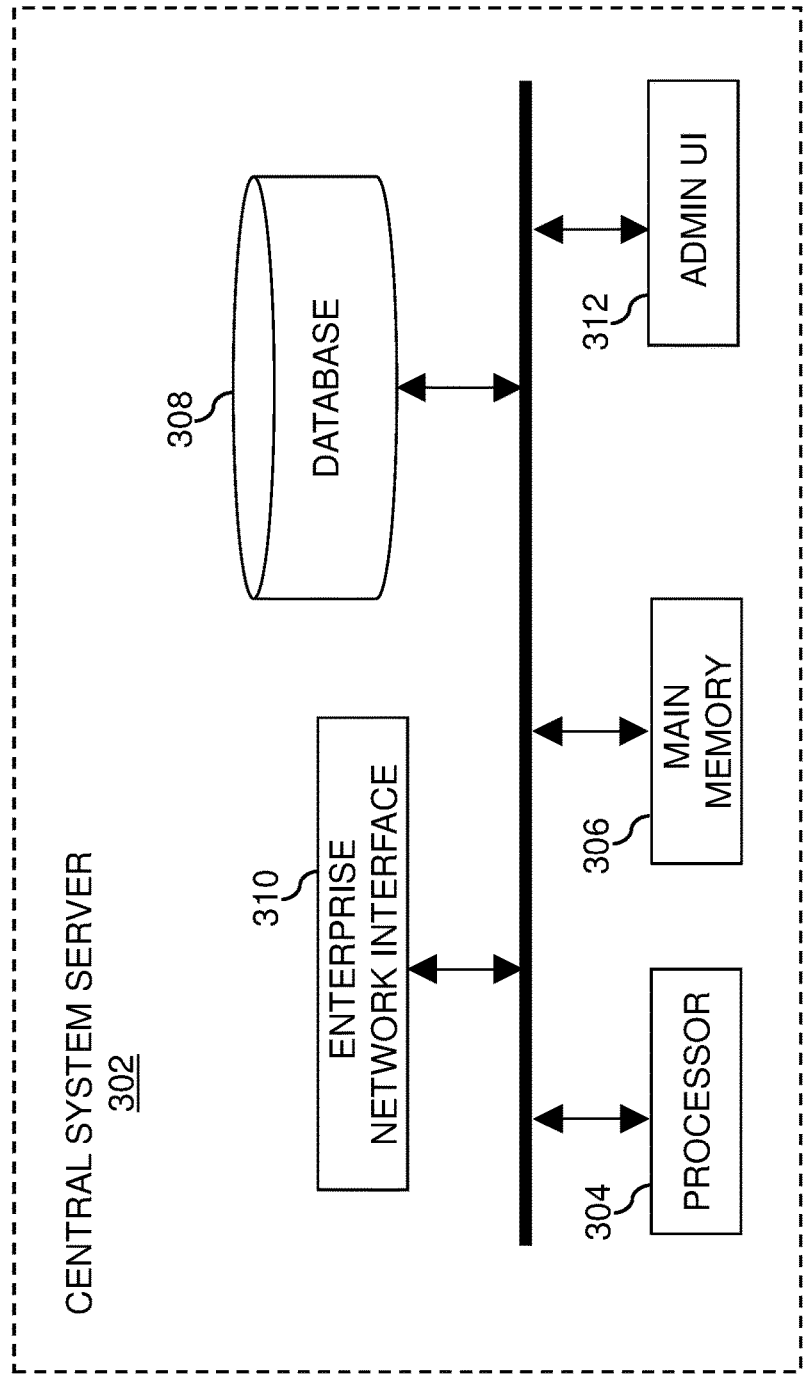
FIG. 3 depicts a block diagram illustrating one embodiment for a central system server that may be included within the central system of FIG. 1 in accordance with embodiments of the present disclosure.

FIG. 3 depicts one embodiment for a central system server 302 that may be included within the central system 106 of FIG. 1 in accordance with embodiments of the present disclosure.

The central system server 302 is a hardware server and may include a processor 304, a main memory 306, a database 308, a datacenter network interface 310, and an administration user interface (UI) 312. The central system server 302 may be configured to host a virtual server. For example, the virtual server may be an Ubuntu® server or the like. The server 200 may also be configured to host a virtual container. For example, the virtual container may be the Docker® virtual container or the like. In some embodiments, the virtual server and or virtual container may be distributed over a plurality of hardware servers using hypervisor technology. The central system server 302 may be implemented in the Microsoft Azure®, the Amazon Web Services® (AWS), or the like cloud computing data center environments. In other embodiments, the central system server 302 may be hosted within the enforcement agency 108.

The processor 304 may be a multi-core server class processor suitable for hardware virtualization. The processor 304 may support at least a 64-bit architecture and a single instruction multiple data (SIMD) instruction set. The main memory 306 may include a combination of volatile memory (e.g. random access memory) and non-volatile memory (e.g. flash memory). The database 308 may include one or more hard drives. The database 308 may be configured to host rule sets and actions (including profiles) for individuals being provided confinement flexibility. In some embodiments, the database 308 may be an open source database such as the MongoDB® database, the PostgreSQL® database, or the like.

The enterprise network interface 310 may provide one or more high-speed communication ports to the data center switches, routers, and/or network storage appliances. The enterprise network interface 310 may include high-speed optical Ethernet, InfiniBand (IB), Internet Small Computer System Interface iSCSI, and/or Fibre Channel interfaces. The administration UI 312 may support local and/or remote configuration of the central system server 302 by a data center administrator and/or an employee of the enforcement agency 108.

Figure 4:
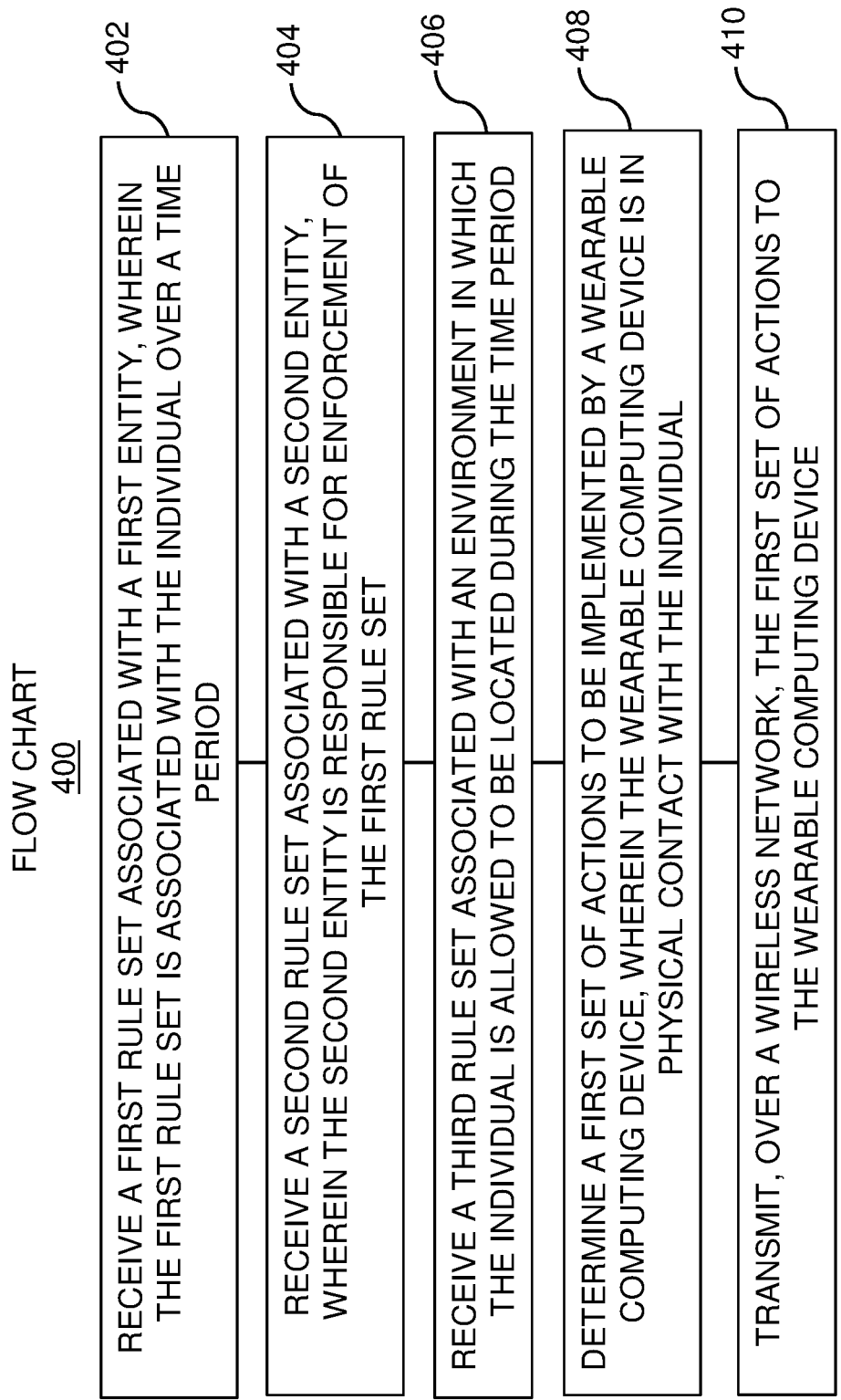
FIG. 4 depicts a flow chart illustrating a method for providing confinement flexibility to an individual in accordance with embodiments of the present disclosure.

FIG. 4 depicts a flow chart 400 disclosing a method including broader embodiments for providing confinement flexibility to an individual in accordance with embodiments of the present disclosure. The method (i.e. steps 402 through 410) may be implemented on one or more computing devices (e.g., the central system server 302). Additionally, the method may be stored as plurality of machine-readable instructions on a non-transitory computer readable medium.

In step 402, the method includes receiving a first rule set associated with a first entity and the first rule set is associated with the individual over a time period. In some embodiments, the first entity may be associated with a judicial branch of government. In further embodiments, the first entity may be associated with a state court system. In other embodiments, the first entity may be associated with a federal court system. In some embodiments, the first rule set may be associated with a criminal sentence imposed on the individual by the judicial branch of government. In further embodiments, the criminal sentence may require incarceration of the individual during the time period. In other embodiments, the first entity may be a family member, a friend, and/or a state agency having legal guardianship responsibility for the individual (e.g., a mentally incapacitated individual).

In step 404, the method further includes receiving a second rule set associated with a second entity and the second entity is responsible for enforcement of the first rule set. In some embodiments, the second entity may be associated with an executive branch of government. In further embodiments, the second entity may be associated with a state corrections system. In other embodiments, the second entity may be associated with a federal corrections system branch of government. In still other embodiments, the second entity may be associated a private corrections system. The private corrections system may be under contract with a state corrections system branch of government and/or a federal corrections system branch of government. In other embodiments, the second entity may be a group home, an institutional care facility, or the like, wherein the individual in mentally incapacitated. In some embodiments the second entity may be an individual having legal guardianship responsibility.

In step 406, the method further includes receiving a third rule set associated with an environment in which the individual is allowed to be located during the time period. In some embodiments, the environment may include a perimeter. The perimeter may be associated with an incarceration of an individual. The first set of actions may include a geometric coordinate located within the perimeter. In some embodiments, the perimeter may approximate a geometric shape. The geometric shape may be a polygon, an oval, or the like. In certain embodiments, the perimeter may have a value between 30 meters and 300 meters. In other embodiments, the perimeter may have a value between 300 meters and 3000 meters. In still other embodiments, the perimeter may have a value between 3000 meters and 30,000 meters. In still other embodiments, the perimeter may have a value less than 30 meters or a value greater than 30,000 meters.

In step 408, the method further includes determining a first set of actions to be implemented by a wearable computing device and the wearable computing device may be in physical contact with the individual. In some embodiments, the first set of actions may include a profile associated with the individual. The profile may include behavioral data and medical data associated with the individual. The behavioral data may include generic behavioral data associated with a personality type and/or individual specific behavioral data associated with the individual. The medical data may include generic medical data associated with a patient type and/or individual specific medical data associated with the individual. The profile may further include environmental data associated with the environment in which the individual is allowed to be located during the time period. In some embodiments, the wearable computing device may include a VR and/or an AR device.

In step 410, the method further includes transmitting, over a wireless network, the first set of actions to the wearable computing device. In some embodiments, the wireless network is a wide area network (WAN). The wireless network may also be a cellular network. The cellular network may include a 3G network, a 4G network, a 5G network, and/or the like. In other embodiments, the wireless network may be a wireless local area network (WLAN). The WLAN may be compliant to at least one version of an Institute of Electrical and Electronics Engineers (IEEE) 802.11 communication standard. In still other embodiments, the wireless network may be a wireless personal area network (WPAN). The WPAN may be compliant to at least one version of a Bluetooth® communication standard.

The method may further include additional steps (not shown in FIG. 4) and implemented on the one of more computing devices after step 408. Additionally, the method may further include receiving a fourth rule set associated with a therapy plan for the individual. The therapy plan may be configured to treat a psychological condition, a behavioral health issue, and/or the like. The therapy plan may allow a therapist that is licensed and/or certified to completely immerse the individual in an AR world and/or VR world that includes social interactions while still providing safety for the therapist, the individual, staff, and the general public. The therapy plan may also be configured to provide a teletherapy session from the therapist. The therapy plan may be further configured to treat at least one category of the Diagnostic and Statistical Manual of Mental Disorders, Fifth Edition, Text Revision (DSM-5-TR). For example, the therapy plan may be configured to treat a trauma and stressor-related disorder, an obsessive-compulsive disorder, and/or an anxiety disorder.

In still additional embodiments, the therapy plan may be configured to treat or reduce symptoms associated with one or more medical disorders (e.g., a brain injury). In still additional embodiments, the therapy plan may be configured to treat sexual disorders (e.g., fetishism, pedophilia, paraphilia, and/or the like). Other embodiments may include treatment of family and/or relationship issues associated with the individual and others. For example, family and/or relationship issues may include self-esteem, abuse (including domestic violence), separation/divorce, and/or the like.

The method may further include additional steps (not shown in FIG. 4) and implemented on the one of more computing devices after step 410. For example, the method may include receiving a proximity alert when the wearable computing device detects a proximity to the perimeter and may include receiving a tamper alert when the wearable computing device detects localized tampering.

The method may also include additional steps not shown in FIG. 4 and not implemented on the one or more computing devices. For example, the method may include attaching the wearable computing device to the individual prior to a beginning of the time period and/or removing the wearable computing device from the individual after an ending of the time period. Additionally, a sworn officer of an executive branch of government may be responsible for attaching and/or removing the wearable computing device to/from the individual.

Figure 5:
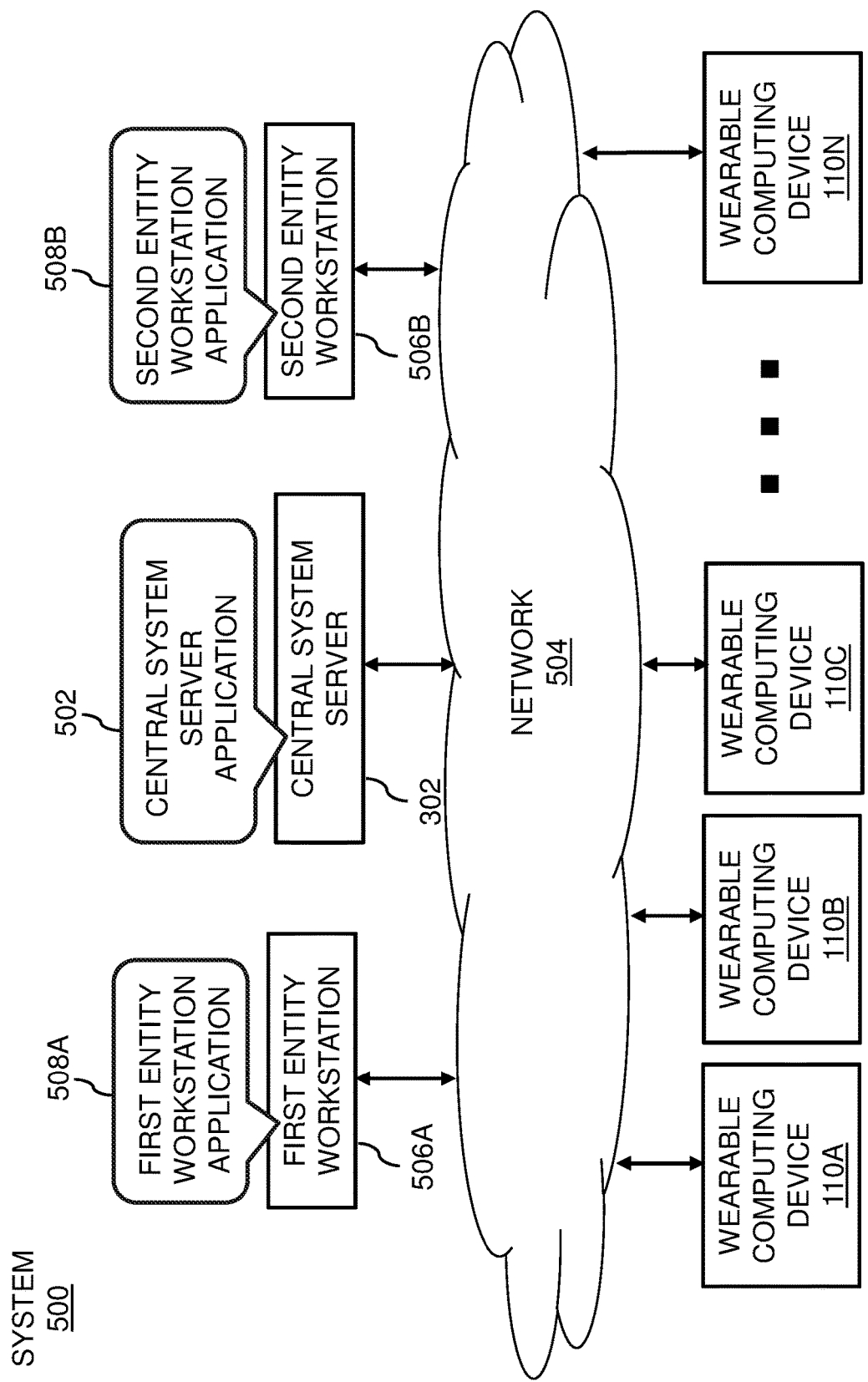
FIG. 5 depicts a block diagram illustrating a further embodiment of the system of FIG. 1 in accordance with embodiments of the present disclosure.

FIG. 5 depicts a block diagram illustrating a system 500 as a further embodiment of the system 102 of FIG. 1 in accordance with embodiments of the present disclosure. The system 500 includes the central system server 302 of FIG. 3 and a plurality of wearable computing devices 110A-110N as described in the block diagram 200 of FIG. 2. The central system server 302 is configured to execute central system server application 502 providing the method of flowchart 400 with each of the plurality of wearable computing devices 110A-110N via a network 506. The network 606 may be any type or combination of wired, wireless, and/or optical networks. The network 606 may include one or more WANs, LANs, and PANs. The network 606 may also include the Internet.

The system 500 also includes a first entity workstation 506A configured to execute a first entity workstation application 508A and a second entity workstation 506B configured to execute a second entity workstation application 508B. The first entity workstation 506A and the first entity workstation application 508A may be associated with the authority in charge 104 of the system 102 of FIG. 1. The second entity workstation 506B and the second entity workstation application 508A may be associated with enforcement agency 108 of the system 102 of FIG. 1. The first entity workstation 508A and the second entity workstation 506B are configured to communicate with the central system server 302 over the network 504.

Figure 6:
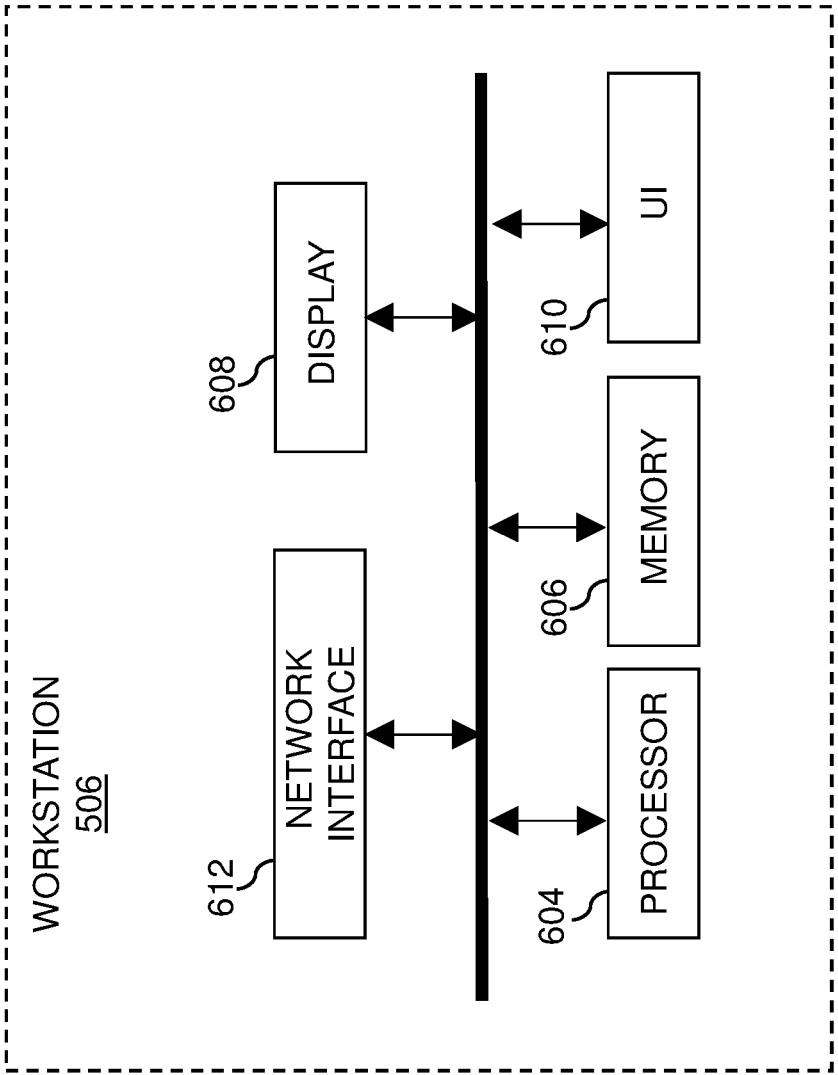
FIG. 6 depicts a block diagram illustrating a workstation of the system of FIG. 5 in accordance with embodiments of the present disclosure.

FIG. 6 depicts a block diagram 600 illustrating the workstation 506 of the system 500 described in FIG. 5 in accordance with embodiments of the present disclosure. The workstation 506 may be configured to communicate with the central system server 302 over the network 504 in a similar manner as described in the system 500 of FIG. 5. The workstation 506 may be configured to host a specific application (e.g., the first entity workstation application 506A and/or the second entity workstation application 506B), a browser application, a third party application, and/or the like. The workstation 510 includes at least one processor 604, a memory 606, a display 608, a user interface (UI) 610, and a network interface 612.

The workstation 510 may include an operating system (OS) such as a Windows® OS, a Macintosh® OS, a Linux® OS, or the like. The memory 606 may include a combination of volatile memory (e.g., random access memory) and non-volatile memory (e.g., solid state drive and/or hard drives). The display 608 may be an external display (e.g., computer monitor) or internal display (e.g., laptop). The UI 610 may include a keyboard, and a pointing device (e.g., mouse). The network interface 612 may be a wired Ethernet interface or a Wi-Fi interface.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module," or "system." Furthermore, aspects of the present invention may take the form of a computer program product (e.g., the method of FIG. 4) embodied in one or more computer readable medium(s) having computer readable program code embodied thereon.

Any combination of one or more computer readable medium(s) may be utilized. The computer readable medium may be a computer readable signal medium or a computer readable storage medium (including, but not limited to, non-transitory computer readable storage media). A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including object oriented and/or procedural programming languages. Programming languages may include, but are not limited to: Ruby, JavaScript, Java, Python, Ruby, PHP, C, C++, C#, Objective-C, Go, Scala, Swift, Kotlin, OCaml, or the like. The program code may execute entirely on the user's computer, partly on the user's computer, as a stand-alone software package, partly on the user's computer, and partly on a remote computer or entirely on the remote computer or server.

Aspects of the present invention are described in the instant specification with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions.

These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the FIGS. illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted, in some alternative implementations, the functions noted in the block may occur out of the order noted in the FIGS. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a," "an" and "the" are intended to include the plural forms as well, unless the context clearly indicates otherwise. Thus, for example, reference to "a user" can include a plurality of such users, and so forth. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method for providing confinement flexibility to an individual, the method comprising:
    using at least one computing device for:
        receiving a first rule set associated with a first entity, wherein:
            the first entity is associated with a judicial branch of government; and
            the first rule set is associated with a criminal sentence over a time period of time imposed on the individual by the judicial branch of government; and
        and
        receiving a second rule set associated with a second entity, wherein:
            the second entity is associated with an executive branch of government; and
            the second entity is responsible for enforcement of the first rule set;
        receiving a third rule set associated with an environment in which the individual is allowed to be located during the time period, wherein the environment includes a perimeter and the perimeter is associated with an incarceration of an individual;
        receiving a fourth rule set associated with a therapy plan for the individual, wherein the therapy plan is configured to treat a psychological condition and a behavioral health issue;
        determining a first set of actions to be implemented by a wearable computing device, wherein:
            the first set of actions is determined based at least partially on the first rule set, the second rule set, the third rule set, and the fourth rule set;
            the first set of actions comprises:
                a geometric coordinate located within the perimeter; and
                a profile associated with the individual, wherein the profile comprises:
                    behavioral data and medical data associated with the individual; and
                    environmental data associated with the environment in which the individual is allowed to be located during the time period;
            the wearable computing device is in physical contact with the individual;
            the wearable computing device includes at least one of a virtual reality (VR) device and an augmented reality (AR) device; and
        transmitting, over a wide area network (WAN), the first set of actions to the wearable computing device.

2. The method of claim 1, wherein the first set of actions includes a geometric coordinate located within the perimeter.

3. The method of claim 1 further comprising using the at least one computing device for receiving a proximity alert when the wearable computing device detects a proximity to the perimeter.

4. The method of claim 1 further comprising using the at least one computing device for receiving a tamper alert when the wearable computing device detects localized tampering.

5. The method of claim 1, wherein the wearable computing device includes a virtual reality (VR) device.

6. The method of claim 1, wherein the wearable computing device includes an augmented reality (AR) device.

7. The method of claim 1 further comprising attaching the wearable computing device to the individual prior to a beginning of the time period by a sworn officer of an executive branch of government.

8. The method of claim 1 further comprising removing the wearable computing device from the individual after an ending of the time period by a sworn officer of an executive branch of government.

9. The method of claim 1 further comprising:
attaching the wearable computing device to the individual prior to a beginning of the time period by a sworn officer of an executive branch of government;
using the at least one computing device for:
receiving a proximity alert when the wearable computing device detects a proximity to the perimeter; and
receiving a tamper alert when the wearable computing device detects localized tampering;
and
removing the wearable computing device from the individual after an ending of the time period by another sworn officer of an executive branch of government.

10. A computing device configured for providing confinement flexibility to an individual, the computing device comprising
a memory; and
a processor configured for:
receiving a first rule set associated with a first entity, wherein:
the first entity is associated with a judicial branch of government; and
the first rule set is associated with a criminal sentence over a time period of time imposed on the individual by the judicial branch of government;
and
and
receiving a second rule set associated with a second entity, wherein:
the second entity is associated with an executive branch of government; and
the second entity is responsible for enforcement of the first rule set;
receiving a third rule set associated with an environment in which the individual is allowed to be located during the time period, wherein the environment includes a perimeter and the perimeter is associated with an incarceration of an individual;
receiving a fourth rule set associated with a therapy plan for the individual, wherein the therapy plan is configured to treat a psychological condition and a behavioral health issue;
determining a first set of actions to be implemented by a wearable computing device, wherein:
the first set of actions is determined based at least partially on the first rule set, the second rule set, the third rule set, and the fourth rule set;
the first set of actions comprises:
a geometric coordinate located within the perimeter; and
a profile associated with the individual, wherein the profile comprises:
behavioral data and medical data associated with the individual; and
environmental data associated with the environment in which the individual is allowed to be located during the time period;
the wearable computing device is in physical contact with the individual;
the wearable computing device includes at least one of a virtual reality (VR) device and an augmented reality (AR) device;
and
transmitting, over a wide area network (WAN), the first set of actions to the wearable computing device.

11. A non-transitory computer readable medium comprising a plurality of machine-readable instructions which when executed by one or more processors of at least one computing device are adapted to perform a method for providing confinement flexibility to an individual, the method comprising:
receiving a first rule set associated with a first entity, wherein:
the first entity is associated with a judicial branch of government; and
the first rule set is associated with a criminal sentence over a time period of time imposed on the individual by the judicial branch of government; and
and
receiving a second rule set associated with a second entity, wherein:
the second entity is associated with an executive branch of government; and
the second entity is responsible for enforcement of the first rule set;
receiving a third rule set associated with an environment in which the individual is allowed to be located during the time period, wherein the environment includes a perimeter and the perimeter is associated with an incarceration of an individual;
receiving a fourth rule set associated with a therapy plan for the individual, wherein the therapy plan is configured to treat a psychological condition and a behavioral health issue;
determining a first set of actions to be implemented by a wearable computing device, wherein:
the first set of actions is determined based at least partially on the first rule set, the second rule set, the third rule set, and the fourth rule set;
the first set of actions comprises:
a geometric coordinate located within the perimeter; and
a profile associated with the individual, wherein the profile comprises:
behavioral data and medical data associated with the individual; and
environmental data associated with the environment in which the individual is allowed to be located during the time period;
the wearable computing device is in physical contact with the individual;
the wearable computing device includes at least one of a virtual reality (VR) device and an augmented reality (AR) device;

and transmitting, over a wide area network (WAN), the first set of actions to the wearable computing device.

12. The method of claim 1, wherein the WAN is a cellular network.

13. The method of claim 12, wherein the cellular network includes at least one of a 3G network, a 4G network, and a 5G network.

14. The method of claim 1, wherein the perimeter approximates a geometric shape.

15. The method of claim 14, wherein the geometric shape is at least one of a polygon and an oval.

16. The method of claim 6, wherein the perimeter has a value between 30 meters and 300 meters.

17. The method of claim 6, wherein the perimeter has a value between 300 meters and 3000 meters.

18. The method of claim 6, wherein the perimeter has a value between 3000 meters and 30,000 meters.

19. The method of claim 1, wherein the second entity is associated with a state corrections system.

20. The method of claim 1, wherein the second entity is associated with a federal corrections system branch of government.

\* \* \* \* \*